United States Patent [19]

Lopez

[11] Patent Number: 4,806,480
[45] Date of Patent: Feb. 21, 1989

[54] NOVEL E. COLI HYBRID PLASMID VECTOR CONFERRING SUCROSE FERMENTING CAPACITY

[75] Inventor: José L. G. Lopez, Madrid, Spain

[73] Assignee: Antibioticos, S.A., Madrid, Spain

[21] Appl. No.: 702,587

[22] Filed: Feb. 19, 1985

[30] Foreign Application Priority Data

Feb. 16, 1984 [GB] United Kingdom ............... 8404057

[51] Int. Cl.$^4$ .................... C12N 1/20; C12N 1/00; C12N 15/00
[52] U.S. Cl. ........................ 435/252.33; 435/320; 435/172.3; 935/29
[58] Field of Search .............. 435/172.3, 253, 317, 435/320; 935/29

[56] References Cited

PUBLICATIONS

Schmidt et al., J. of Bacteriol, 151: 68–76, Jul. 1982.
Prentki et al., Gene 4: 289–299, 1981.
Maniatis et al., Molecular Cloning a Laboratory Manual, Cold Spring Harbor, p. 505 (1982).

Primary Examiner—Alvin E. Tanenholtz
Attorney, Agent, or Firm—Finnegan, Henderson, Farabow, Garrett & Dunner

[57] ABSTRACT

A new hybrid plasmid vector suitable for transforming microorganisms of the genus Escherichia. This plasmid vector confers sucrose fermenting capacity to E. coli K12 cells. The plasmid vector may also be useful for carrying additional genetic information capable of controlling the production of commercially useful chemical compounds. Fermentation cultures of the microorganisms containing this plasmid vector may be propagated in a medium containing sucrose as the main carbon source, thereby increasing the plasmid stability.

3 Claims, 1 Drawing Sheet

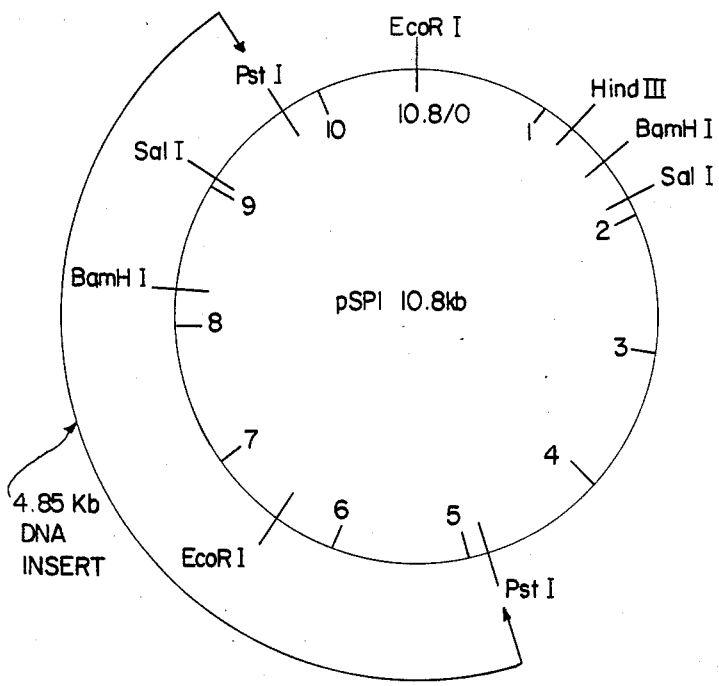

NOVEL E. COLI HYBRID PLASMID VECTOR CONFERRING SUCROSE FERMENTING CAPACITY

BACKGROUND OF THE INVENTION

It is well-known that microorganisms of *Escherichia coli* K12 strains are some of the preferred microorganisms for carrying out genetic engineering experiments. *E. coli* K12 strains have been preferred mainly for two reasons: first, the genetic make-up of these organisms is well-known, and, second, recombinant DNA guidelines from several countries insist on the use of this strain to carry out recombinant experiments. As a result, recombinant DNA technology has been developed to produce, on an industrial level, commercially interesting substances using the host-vector system of *E. coli* K12.

However, *E. coli* K12 strains do not have the sucrose fermenting capacity that other industrially successful microorganisms, such as Bacillus, Corynebacterium, Actinomyces and yeasts, have. Therefore, *E. coli* K strains cannot grow efficiently using raw materials, such as molasses, which contain sucrose as the main carbon source.

As a result of the preferences for using *E. coli* K12, an *E. coli* plasmid vector has been sought which could be used to confer sucrose fermenting characteristics to such microorganisms. In such circumstances, this plasmid would additionally have the ability to carry industrially profitable genetic information.

Such a plasmid vector would afford an additional advantage in assuring the stability of a culture of microorganisms containing this vector. Such stability would arise as a result of expression of the sucrose fermenting phenotype; when a culture medium with sucrose as the carbon source is utilized, only the cells carrying the plasmid are able to grow and multiply, as they alone would have the ability to ferment sucrose. In other words, if the cells were to lose the plasmid containing the commercially useful genes, they would also lose their sucrose fermenting capacity and would not be able to grow in the provided culture medium. This plasmid-mediated stability avoids the expense of the addition of large amounts of antibiotics to the culture medium to assure plasmid stability.

SUMMARY OF THE INVENTION

Accordingly, it is an object of this invention to construct a plasmid vector which contains genetic material capable of providing a microorganism possessing industrially useful capabilities. A further object of this invention is to provide a plasmid vector which additionally confers sucrose fermenting capacity in a host organism.

Additionally, an object of the present invention is to provide a microorganism culture wherein microorganisms containing an industrially useful plasmid are capable of growth while other microorganisms, which do not contain such a plasmid, are not capable of growth.

To accomplish these objects and to further the purposes of the present invention, a plasmid vector incorporating a DNA fragment capable of conferring sucrose fermenting capacity upon host cells is transformed into a strain of *E. coli* K12 to construct a novel microorganism. Preferably, *E. coli* K12 DH1, described in *Molecular Cloning*, Cold Spring Harbor (1982), serves as a host organism.

These newly constructed microorganisms are capable of growth in a culture medium containing sucrose as the sole carbon source. If the plasmid is eliminated from the cells, then the cells would lose their ability to metabolize sucrose and would become incapable of growth in such a medium.

When *E. coli* K12 DH1 cells are used as a host organism, the novel organism which is created is *E. coli* K12 DH1 (pSP1). *E. coli* K12 DH1 (pSP1) is on deposit at The National Collections of Industrial and Marine Bacteria, Aberdeen, Scotland under Accession No. NCIB 11940. Transformed *E. coli* DH1 cells carrying the plasmid vector can grow efficiently in raw materials containing sucrose as a main carbon source, such as molasses.

To further achieve the objects and in accordance with the purposes of the present invention, a novel hybrid plasmid vector pSP1 is disclosed. Plasmid vector pSP1 has the entire nucleotide sequence of plasmid pBR325 and a foreign DNA insert at the PstI site. The plasmid vector has a molecular weight of about 10.8 kb.

These plasmid vectors can be used to incorporate other genes of industrial interest into *E. coli* strains. The sucrose fermenting capacity conferred by the plasmid vector is useful not only to permit the growth of the microorganism in sucrose-containing media, but also to increase the plasmid stability when the fermentation is conducted without the addition of antibiotics to the media. Moreover, if other, undesired microorganisms are present in the culture, it is possible to add an antibiotic to the medium for which the plasmid vector confers resistance, thereby further increasing the plasmid stability by eliminating the undesired microorganism. As a result, the microorganism and the plasmid vectors of the present invention are of great utility in commercial fermentation processes.

Additionally, to achieve the objects and in accordance with the purposes of the present invention, plasmid vectors are disclosed which are suitable for transformation into appropriate host microorganisms, which plasmid vectors contain the foreign DNA insert present in plasmid pSP1.

DESCRIPTION OF THE PREFERRED EMBODIMENTS

The preferred host microorganism used in this invention is the strain of *Escherichia coli* K DH1 described in *Molecular Cloning*, Cold Spring Harbor (1982). However, other *E. coli* strains may be used with good results.

To create the plasmid vector of the present invention, sucrose fermenting genes, hereinafter referred to as the sucrose operon, are obtained. Preferably, the sucrose operon is obtained from DNA of *E. coli* strain AB1281 (scr53). This strain has been described by Wohlhieter, J.A. et al., in *J. Bacteriol.* 122: 401–406 (1975), specifically incorporated herein by reference, and is on deposit at the National Collections of Industrial and Marine Bacteria, Aberdeen, Scotland under Accession No. NCIB 11993. This strain carries the conjunctive plasmid scr53 (53 Mdal) which was found to confer sucrose fermenting properties to a clinically isolated Salmonella strain. The scr53 plasmid containing the sucrose operon can be used to transfer, by conjugation or transduction, the sucrose fermenting capacity to other Salmonella or *Escherichia coli* strains, but is unsuitable for use as a cloning plasmid vector for genetic experiments.

To construct the preferred plasmid vector of the present invention, the sucrose operon contained in the scr53 plasmid was subcloned into a suitable plasmid vector. After extraction of the scr53 plasmid DNA by conventional procedures, the recovered DNA was treated with a restriction endonuclease. Any plasmid or phage which can propagate in microbial cells of Escherichia may be employed as the vector DNA. After digesting the vector DNA with a restriction endonuclease, the scr53 fragment DNA is inserted into the vector using any conventional technique suitable for preparing recombinant DNA products. The hybrid plasmid thus obtained can be incorporated into a microorganism of the genus Escherichia by conventional transformation techniques, although the efficiency of the transformation process may differ according to the technique utilized.

Transformants are easily selected since colonies carrying the transformed plasmid vector are capable of growth in a medium with sucrose as the sole carbon source and may have additional markers in the vector which may be suitable for demonstrating antibiotic resistance.

Plasmids thus engineered according to the present invention confer upon a transformant the genetic information necessary for fermentation processing together with the sucrose fermenting capability. This causes transformants to grow suitably in sucrosecontaining media, such as molasses, and the sucrose operon therefore contributes to the maintenance of plasmid stability.

The sucrose operon identified by this method may be subcloned in other plasmid vectors of a broad host range, such as the RSF1010 plasmid, which can be useful to confer, by transformation, the sucrose fermenting capacity to other gram negative bacteria.

Having generally described the invention, a more complete understanding may be obtained by reference to certain specific examples, which are provided herein for purposes of illustration only and are not intended to be limiting unless otherwise specified.

EXAMPLE

A. Preparation of the scr53 plasmid DNA possessing genetic information responsible for sucrose fermenting characteristics.

Escherichia coli AB1281 (scr53) carrying the scr53 conjugative plasmid, as described in Wohlhieter et al., supra, and on deposit under NCIB Accession No. 11993, was cultured at 37° C. for 16 hours with shaking in 500 ml of L medium containing 1% peptone, 0.5% yeast extract, 0.5% NaCl and 0.1% sucrose, adjusted to pH 7.2. Bacterial cells were collected and plasmid DNA was extracted according to the method of Hansen and Olsen, J. Bacteriol. 135: 227 (1978), specifically incorporated herein by reference. The scr53 plasmid was further purified by isopycnic centrifugation in CsCl in presence of ethidium bromide. Ten micrograms of purified DNA were obtained.

B. Preparation of vector DNA.

Vector DNA was prepared from plasmid pBR325, a vector containing ampicillin, tetracycline and chloramphenicol resistance genes as markers. Plasmid pBR325 has been described in Gene 4: 121 (1978), specifically incorporated herein by reference. Vector DNA was prepared by incubating Escherichia coli K12 DH1 cells containing the pBR325 plasmid at 37° C. in 500 ml of L broth (1% peptone, 0.5% yeast extract, 0.5% NaCl, adjusted to pH 7.2) containing 100 micrograms/ml of ampicillin. Exponential phase cultures were amplified with 300 micrograms/ml of spectinomycin. After 16 hours of incubation, the cells were harvested and lysed by treatment with lysozyme and SDS, as set forth in Biochim. BiophYs. Acta 299: 516 (1973), specifically incorporated herein by reference. After purification by CsCl-Ethidium bromide equilibrium density gradient centrifugation, 500 micrograms of plasmid DNA were obtained.

C. Insertion of the scr53 plasmid DNA fragment into vector DNA.

One microgram of the scr53 plasmid DNA and two micrograms of the vector DNA were each treated with restriction endonuclease PstI at 37° C. for 1 hour to cleave the DNA chains, then heated at 65° C. for 10 minutes.

The digested scr53 plasmid DNA and the vector DNA solutions were mixed and incubated with T4 phage DNA ligase in the presence of ATP, $MgCl_2$ and dithiothreitol at 14° C. for 24 hours. The resultant recombinant DNA was rcovered by ethanol precipitation.

D. Genetic transformation with the hybrid plasmid containing the genetic information responsible for sucrose fermenting character.

Escherichia coli DH1 competent cells were prepared by the RbCl method described by Hanahan, J. Mol. Biol. 166: 557 (1983), specifically incorporated herein by reference. The hybrid plasmids obtained in step (C) above were added to the suspension of competent cells. The resultant mixture was kept in ice for 20 minutes, heated to 37° C. for 2 minutes, and allowed to stand again in ice for 60 seconds to allow transformation.

The transformed cells were inoculated into L broth and the medium was shaken at 37° C. for 1 hour to complete the transformation reaction. The cells were collected and washed with saline solution (NaCl 8.5 g/1) and plated on agar medium (9 g $K_2HPO_4$, 4.5 g $KH_2PO_4$, 2 g $(NH_4)_2 SO_4$, 0.1 g $MgSO_4$ $7H_2O$, 0.1 g $FeSO_4$ $7H_2O$, thiamine-HCl 1 mg, 5 g sucrose, 15 g agar per liter and 12.5 microgram/ml of tetracycline). The plates were incubated at 37° C. for two days. At the end of the incubation period, 8,000 colonies were counted on the plates. One hundred colonies were picked, purified and isolated.

Every transformant thus obtained was screened for its sucrose fermenting capacity (scr+phenotype) using a medium containing 10 g peptone, 5 g NaCl, 10 g sucrose, 0.02 g bromocresol purple and 15 g of agar per liter. In this medium, sucrose fermenting transformants appeared as yellow colonies. The transformants were also screened for tetracycline and chloramphenicol resistance and ampicillin sensitivity.

The plasmids of the cells presenting the appropriate phenotype (scr+, $Cm_R$, $Tc^R$, $Ap^S$) were analyzed by the minipreparation method as described in Molecular Cloning, Cold Spring Harbor Laboratory (1982), specifically incorporated herein by reference. The hybrid plasmids were digested by PstI and a plasmid with a PstI insert of 4.85 Kb was selected. The hybrid plasmid contain ing the insert was named pSPl. The hybrid plasmid had a total size of 10.8 Kb.

E. Preparation of pSPl plasmid.

Escherichia coli DH1 (pSPl) (AM512), NCIB Accession No. 11940, sucrose fermenting cells carrying the pSPl plasmid were used to extract the pSPl plasmid DNA by the same procedure described in step (B).

F. Cleavage sites for various restriction endonucleases of the pSP1 plasmid.

In this step, 0.5 micrograms of pSP1 plasmid DNA prepared by the above method was digested with the following restriction endonucleases:

| EcoRI | Escherichia coli |
|---|---|
| HindIII | Haemophillus influenzae |
| PstI | Providencia stuartii |
| SalI | Streptomyces albus |
| BamHI | Bacillus amyloliquefaciens |
| XbaII | Xanthomonas badrii |
| PvuII | Proteus vulgaris |
| ClaI | Caryophanum latum |
| XhoI | Xanthomonas holicola |
| HincII | Haemophilus influenzae |
| SphI | Streptomyces phaechromogenes |
| SmaI | Xanthomonas malvacearum |
| BglII | Bacillus globigii |

The restriction endonucleases were obtained from Biolab New England Inc. and Boehringer Mannheim GmbH, and were used under suitable conditions for each enzyme. The resulting DNA fragments were analyzed by horizontal electrophoresis in 0.7% agarose gel. The molecular weight of each fragment was determined from the electrophoretic mobility. The molecular weight was estimated based on a standard curve plotted against electrophoretic mobility of DNA fragments of known molecular weight, derived from HindIII digestion of and $\phi_{29}$ phage DNAs.

The results are illustrated in Table 1. The restriction map of the pSP1 plasmid was constructed by single and double digestions of the plasmid DNA with restriction endonucleases, analyzing the DNA fragments by agarose gel electrophoresis. The known restriction endonuclease map of pBR325, as described in Gene 14: 289 (1981), specifically incorporated herein by reference, was also used to determine the pSP1 restriction map which is shown in FIG. 1.

TABLE 1

| Restriction endonuclease enzyme | Number of cleavage sites of pSP1 plasmid |
|---|---|
| BglII | 0 |
| XbaI | 0 |
| XhoI | 0 |
| SmaI | 1 |
| HindIII | 1 |
| ClaI | 2 |
| BamHI | 2 |
| EcoRI | 2 |
| SalI | 2 |
| PstI | 2 |
| SphI | 2 |
| HincII | 5 |
| PvuII | 5 |

G. Analysis of the sucrose cleaving enzyme.

Sucrose activity was determined by a method based on the reduction of sugars after sucrose splitting. The method involved the use of E. coli DH1 cells containing the pBR325 plasmid or the new hybrid vector plasmid pSP1, grown in L broth and in L broth containing 10 mM sucrose. Cells were harvested and bacterial pellets washed with 50 mM potassium phosphate buffer, pH 6.5, containing 200 mM KCl, 1 mM 2-mercaptoethanol. After washing, the cells were resuspended in the same buffer and sonicated. The sonicated suspension was centrifuged at 40,000 g for 20 minutes at 4° C. The supernatant was extracted and used without further treatments. A mixture of 0.5 ml of the enzyme preparation and 0.5 ml of 1M sucrose was incubated for 30 minutes at 37° C. Reaction was stopped by the addition of 1 ml of dinitrosalicilic reagent as described in *Methods in Enzymol.* 1: 149 (1955), specifically incorporated herein by reference. Samples were placed in a boiling water bath for 5 minutes, cooled in ice and diluted with 20 ml of distilled water. Optical densities of samples were determined at 540 nm. Standard solutions of glucose were used as controls. Protein concentration was determined by a conventional method.

Sucrose activity was demonstrated in the E. coli DH1 pSP1 containing cells as shown in Table 2.

TABLE 2

| Strain | Plasmid | growth in minimal salt medium M63 + thiamine + 0.5% sucrose | sucrose fermenting phenotype | sucrose activity mg of reducing sugar/30 mg of protein | |
|---|---|---|---|---|---|
| | | | | L broth | L broth 10 mM sucrose |
| E. coli DH1 | pBR325 | — | scr− | 0.0 | 0.0 |
| E. coli DH1 | pSP1 | + | scr+ | 1.4 | 1.4 |

What is claimed is:

1. Escherichia coli DH1 (pSP1) having the Accession No. NClB 11940.

2. Hybrid plasmid vector pSP1 wherein said plasmid has nucleotide sequence of plasmid pBR325 and a foreign DNA insert at the PstI site of pBR325, said DNA insert being the 4.85 kb fragment of plasmid pSP1 shown in FIG. 1, and wherein said plasmid has a molecular weight of about 10.8 kb and the following cleavage sites for restriction endonucleases:

| Restriction enzyme | Number of cleavage sites |
|---|---|
| BglII | 0 |
| XbaI | 0 |
| XhoI | 0 |
| SmaI | 1 |
| HindIII | 1 |
| ClaI | 2 |
| BamHI | 2 |
| EcoRI | 2 |
| SalI | 2 |
| PstI | 2 |
| SphI | 2 |
| HincII | 5 |
| PvuII | 5 |

3. Plasmid vector which comprises RSF1010 plasmid and a DNA insert consisting essentially of the 4.85 fragment of plasmid pSP1 shown in FIG. 1.

* * * * *